United States Patent [19]

Bulot

[11] Patent Number: 4,743,603

[45] Date of Patent: May 10, 1988

[54] DERIVATIVES OF 2-(3-PYRIDYL)-2-PHENYLAMINOACETIC ACID AND THEIR USE AS ANTIFUNGALS IN THE FIELD OF ARGRICULTURE

[75] Inventor: Jean P. Bulot, Dardilly, France

[73] Assignee: Rhone-Poulenc Agrochimie, Lyons, France

[21] Appl. No.: 867,786

[22] Filed: May 27, 1986

Related U.S. Application Data

[63] Continuation-in-part of Ser. No. 670,318, Nov. 13, 1984, abandoned.

[30] Foreign Application Priority Data

Nov. 24, 1983 [FR] France ............... 83 18976

[51] Int. Cl.$^4$ .................. A01N 43/40; C07D 213/63; C07D 213/55; C07D 213/57
[52] U.S. Cl. .......................... 514/235.5; 514/252; 514/318; 514/340; 514/343; 514/346; 514/348; 514/351; 514/357; 514/212; 546/194; 546/275; 546/281; 546/291; 546/296; 546/300; 546/335; 546/337; 544/124; 544/131; 544/360; 544/365
[58] Field of Search ............... 546/291, 337, 296, 300, 546/330, 335, 194, 281, 275; 514/346, 351, 348, 357, 318, 228, 343, 233, 340, 252; 544/124, 131, 360, 365

[56] References Cited

U.S. PATENT DOCUMENTS

3,313,683  4/1967  Taylor ................. 514/331

OTHER PUBLICATIONS

Streitwieser, A. et al., "Introduction To Organic Chemistry", MacMillan Publishing Co., N.Y. (1976), pp. 1206, 1208.
March, J., "Advanced Organic Chemistry", Second Edition, McGraw-Hill, N.Y. (1977), p. 875.
Merck Index, Ninth Edition (1976), p. ONR-80.
Walia, J. S., et al., Chemical Abstracts, vol. 68, p. 6610, 68602g (1968).

Primary Examiner—Henry R. Jiles
Assistant Examiner—Dale A. Bjorkman
Attorney, Agent, or Firm—Scully, Scott, Murphy & Presser

[57] ABSTRACT

New derivatives of 2-(3-pyridyl)-2-phenylaminoacetic acid, of the formula:

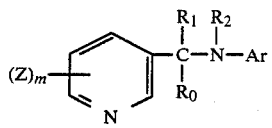

with:
  $R_0$: —CN, —COOH, $CONH_2$, $COOR_4$,
  $R_1$: H, lower alkyl, cycloalkyl, phenyl, if appropriate substituted, aralkyl if appropriate substituted,
  $R_2$: H, lower alkyl, if appropriate substituted,
  Ar: phenyl if appropriate substituted,
  Z: halogen, lower alkyl, lower alkoxy, lower alkylthio.

They can be employed in agriculture for combating phytopathogenic fungi such as the sclerotiniaceae.

15 Claims, No Drawings

DERIVATIVES OF 2-(3-PYRIDYL)-2-PHENYLAMINOACETIC ACID AND THEIR USE AS ANTIFUNGALS IN THE FIELD OF ARGRICULTURE

This application is a continuation-in-part of Ser. No. 06/670,318, filed Nov. 13, 1984, now abandoned.

The present invention relates to new derivatives of 2-(3-pyridyl)-2-phenylaminoacetic acid, their preparation and their use for plant protection, against phytopathogenic fungi.

One aim of the invention is the provision of products for use in plant protection having an outstanding activity towards phytopathogenic fungi of the sclerotiniaceae type, particularly botrytis.

Another aim of the invention is to provide fungicides possessing additionally activity towards other phytopathogenic fungi responsible for crop diseases, such as the fungal diseases of cereals (root rot, septorioses, mildew, rusts), the cercosporioses and diseases of fruit trees.

Another aim of the invention is to provide fungicides possessing additionally activity towards other phytopathogenic fungi responsible for rice diseases such as rice blast.

It has now been found that these aims could be attained by virtue of the products of the invention.

The products of the invention correspond to the general formula (I).

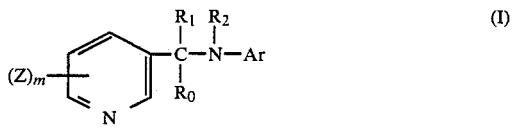

in which $R_0$ denotes a radical chosen from the radicals —CN, —COOH, —CONH$_2$ and the radical —COOR$_4$ in which R$_4$ denotes a lower alkyl radical.

$R_1$ denotes the hydrogen atom or a lower alkyl radical, optionally substituted, (e.g. by one or more substituents chosen from halogen atoms and lower alkoxy radicals and lower alkylthio radicals) or a cycloalkyl radical containing from 3 to 7 ring members (e.g. cyclopropyl, cyclobutyl, cyclopentyl, cyclohexyl) optionally substituted, or a phenyl radical itself optionally substituted (e.g. by one or more halogen atoms or lower alkyl radicals) or aralkyl radical optionally substituted (e.g. benzyl or phenylethyl optionally substituted by 1 or more halogen atoms), $R_2$ denotes the hydrogen atom or a lower alkyl radical optionally substituted, (e.g. by one or more halogen and lower alkoxy or alkylthio), provided that $R_1$ and $R_2$ do not simultaneously denote the hydrogen atom, Z denotes a halogen atom or a lower alkyl radical, lower alkoxy radical or lower alkylthio radical, m is an integer from 0 to 4, including the limits, it being understood that when m is greater than 1 the substituents Z may be either identical or different, Ar denotes a phenyl radical optionally substituted, e.g. by one or more substituents chosen from halogen atoms, lower alkyl radicals and lower cycloalkyl radicals themselves optionally substituted, (e.g. by one or more halogen atoms or one or more hydroxy, lower alkoxy, lower alkylthio radicals), lower alkenyl (mono- or polyunsaturated) radicals themselves optionally substituted (e.g. by one or more halogen atoms), lower alkoxy radicals themselves optionally substituted (e.g. by one or more halagen atoms), lower alkylthio radicals themselves optionally substituted (e.g. by one or more halogen atoms), cyano, nitro, hydroxy, carboxyle, lower alkoxycarbonyl radicals, carbamoyl, N-alkyl carbamoyle, N,N-dialkyl carbamoyle, N-piperidinyl carbonyl, N-pyrolidinyl carbonyl, N-azepinyl carbonyl, N-morpholinyl carbonyl, N-1 piperazinyl carbonyl radicals, phenyl radical optionally substituted.

As used in the present text, the adjective "lower", when qualifying an organic radical means that this radical contains at most 6 carbon atoms. This radical may be either linear or branched.

Those compounds according to formula (I) in which $R_0$ denotes a —CN or —COOR$_4$ or —CONH$_2$ group can form various addition salts with suitable acids which may be inorganic, such as e.g. hydrochloric acid, sulphuric acid or phosphoric acid, or organic acids such as e.g. succinic acid, fumaric acid, maleic acid, oxalic acid or tartaric acid. Moreover, those compounds according to formula (I) in which $R_0$ denotes a —COOH group can give salts with suitable bases. These various salts are included within the scope of the present invention, most particularly when they are agriculturally acceptable (i.e. acceptable for the plants treated).

They may be prepared according to methods which are known per se, e.g. by dissolving the compound (I) in a suitable solvent, then by reacting with a suitable acid or base (according to the meaning of $R_0$).

The compounds according to formula (I) all contain an asymmetrically substituted carbon atoms situated in the alpha position relative to the pyridyl group. As a result of this each of the compounds according to the formula (I) can exist in stereoisomeric forms, whose antifungal activity levels can differ from each other. These stereoisomeric forms, as well as their mixtures, optically active or racemic, are also included within the scope of the present invention.

Various heterocyclic derivatives of acetonitrile have already been described:

Thus, European Patent Application EP-A, 48,039 describes derivatives of 2-phenylaminoacetonitrile substituted in the 2 position of acetonitrile by a heterocyclic radical necessarily containing 5 ring members. According to this reference, these compounds can be employed as plant growth regulators.

European Patent Application EP-A 8,145 and its American equivalent U.S. Pat. No. 4,281,134 describe, as plant growth regulators and fungicides, various derivatives of phenyliminopyridine. The periodical Chem. Ind. (London) 1968 (5) p. 155 (Chemical Abstracts 68 No. 68,602 g) describes derivatives of 2-phenylaminoacetonitrile which are substituted in the 2 position on acetonitrile by a 2-pyridyl, 2-furyl or 2-thienyl radical (excepting any 3-pyridyl radical). No use is mentioned for these compounds.

German Patent Application DE-A 1,026,318 describes several 2-dialkylamino-3-(2-pyridyl)acetonitriles which can be employed as medicaments.

Finally, moreover, American Patent U.S. No. 3,313,683 mentions in a general manner a very extensive family of acetonitrile derivatives, including 2-arylamino-2-arylacetonitriles, 2-alkylamino-2-arylacetonitriles and 2-dialkylamino-2-arylacetonitriles. However, it describes only a single derivative of 2-(3-pyridyl)acetonitrile, different from those claimed by the present Patent Application and indicates that these compounds are active both as nematocides and as fungicides active against soil fungi such as *Rhizoctonia solani, Fusarium oxysporum* and *Sclerotium rolfsii.*

The compounds according to the invention are different from those described in the various documents referred to above. Their outstanding antifungal properties, especially towards Botrytis for all compounds and towards powdery mildew of Barley, brown rust of wheat, rice blast for some could not be expected when this prior art is taken into account.

Among the compounds according to the formula (I), the invention relates more especially to the compounds corresponding to the formula (II):

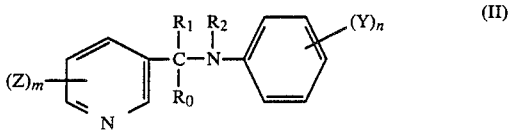

and the agriculturally acceptable salts of these compounds (II).

In the formula (II):

$R_0$ denotes the —CN group or the —COOR$_4$ group in which R$_4$ denotes a lower alkyl radical $R_1$ denotes a lower alkyl radical or lower cycloalkyl radical, $R_2$ denotes the hydrogen atom or the methyl radical, m is an integer equal to 0, 1 or 2

Z denotes an alkyl or alkoxy radical containing from 1 to 3 carbon atoms, it being understood that when m is equal to 2 the substituents Z may be identical or different n is an integer equal to 0, 1, 2, 3 or 4

Y denotes a halogen atom (e.g. fluorine, chlorine or bromine) or an alkyl radical containing from 1 to 3 carbon atoms (e.g. methyl), a haloalkyl containing from 1 to 3 carbon atoms (e.g. trifluoromethyl), an alkoxy radical containing from 1 to 3 carbon atoms (e.g. methoxy), an halogen substituted alkoxy containing from 1 to 3 carbon atoms (e.g. trifluoromethoxy), an alkylthio radical containing from 1 to 3 carbon atoms (e.g. methylthio), an halogen substituted alkylthio containing from 1 to 3 carbon atoms (e.g. trifluoromethylthio), or a lower alkoxycarbonyl, phenyl or lower cycloalkyl radical (e.g. cyclohexyl).

Among the compounds corresponding to the formula (II) a sub-group which is preferred in view of its antifungal effectiveness towards Botrytis consists of the compounds in which:

$R_0$ has the same meaning as in the formula (II)

$R_1$ denotes an alkyl radical containing from 1 to 5 carbon atoms, $R_2$ denotes the hydrogen atom, n is equal to 1 or 2

Y denotes a fluorine, chlorine or bromine atom it being understood that when n is equal to 2, the atoms Y may be identical or different.

m is equal to 0, 1 or 2

Z denotes a methyl or ethyl or methoxy radical.

Preferably one of the halogen atoms Y is in position 4 of the phenyl ring.

Among the compounds according to the formula (II), a sub-group which is preferred in view of its antifungal effectiveness towards powdery mildew of Barley consists of the compounds in which:

$R_0$ has the same meaning as in the formula (II)

$R_1$ denotes an alkyl radical containing from 1 to 5 carbon atoms, $R_2$ denotes the hydrogen atom, n is equal to 1 or 2, Y denotes a fluorine, chlorine or bromine atom, or an halogen substituted alkoxy or alkylthio radical (e.g. trifluoromethoxy or trifluoromethylthio), it being understood that when n is equal to 2, the atoms Y may be identical or different.

m is equal to 0, 1 or 2,

Z denotes a methyl or ethyl or methoxy radical.

Preferably one of the atoms Y is in position 4 of the phenyl ring.

Among the compounds according of the formula (II), a sub-group which is preferred in view of its antifungal effectiveness towards brown rust of wheat and rice blast consists of the compounds in which:

$R_0$ has the same meaning as in the formula (II)

$R_1$ denotes an alkyl radical containing from 1 to 5 carbon atoms $R_2$ denotes the hydrogen atom n is equal to 1, 2, 3, 4, preferably 1 or 2, Y has the same meaning as in the formula (II) on condition that at least one of the Y is an halogen substituted alkoxy or alkylthio radical (e.g. trifluoromethoxy or trifluoromethylthio). Preferably said radical is in position 4 of the phenyl ring.

It is pointed out that these results are totally unexpected in view of the anti-Botrytis properties of compounds of formula (I).

It must be added moreover that it is necessary to have an halogen substituted alkoxy or alkylthio radical to obtain this property.

The present invention moreover relates to the preparation of the compounds corresponding to the formula (I).

The compounds according to the formula (I) in which $R_0$ denotes the —CN group may be obtained according to a first process by reacting the pyridine derivative of formula (III):

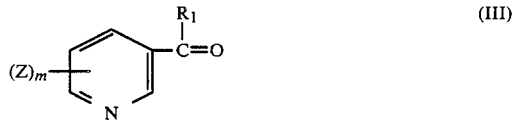

in which $R_1$, Z and m have the same meaning as in formula I, with the aniline derivative of formula (IV):

in which Ar and $R_2$ have the same meaning as in formula (I), by operating in the presence of hydrocyanic acid, formed "in situ" if appropriate.

The reaction is carried out advantageously at a temperature of the order of 0° to 100° C., optionally in the presence of a solvent which is inert (i.e. does not react with the reactants present under the conditions of the reaction). This solvent may advantageously be chosen from aromatic or aliphatic or cycloaliphatic hydrocarbons, these hydrocarbons being if appropriate halogenated, such as e.g. toluene, xylenes, chlorobenzene, dichlorobenzenes and the like. Other inert solvents may also be employed without departing from the scope of the invention.

According to an embodiment of the invention, hydrocyanic acid is added to the reaction medium, in the form of a solution, or in gaseous form, or in liquid form by operating under pressure.

Preferably, hydrocyanic acid is formed "in situ" in the reaction medium, by reacting a suitable acid with an alkali metal cyanide. The acid may be an inorganic acid, such as e.g. hydrochloric acid or an organic acid, such as e.g. acetic acid, which may then be employed both as reactant and as solvent.

Advantageously, this formation in situ is obtained by reaction of acetic acid with an aqueous solution of potassium cyanide.

The compounds according to the formula (I) in which $R_0$ denotes the —CN group can also be obtained according to a second process.

This process is characterized in that it consists: of a first stage for reacting the pyridine derivative of formula (III)

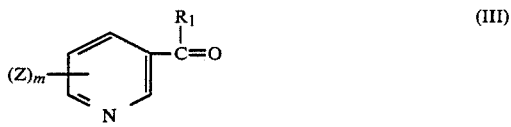

in which $R_1$, Z and m have the same meaning as in the formula (I), with the aniline derivative of formula (V)

$H_2N—Ar$ (V)

in which Ar has the same meaning as in the formula (I), to give the 3-phenyliminomethylpyridine derivatives of formula (VI)

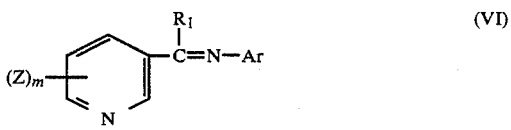

in which $R_1$, Z, m and Ar have the same meaning as in the formula (I), then of a second stage to react hydrocyanic acid if appropriate formed in situ, with this 3-phenyliminomethylpyridine derivative of formula (VI).

Advantageously the first stage of this process is carried out at a temperature of the order of 20° C. to 150° C. in a solvent which is inert (i.e. unreactive towards the reactants present), in the presence of an usual dehydrating agent, such as a strong acid (e.g. sulphuric acid, or p-toluenesulphonic acid) or an acid anhydride or chloride (e.g. $P_2O_5$ or $POCl_3$) or a Lewis acid. Preferably water is removed from the reaction medium by azetropic distillation. As solvent which may be employed for this first stage, mention can be made of aromatic, or aliphatic, or cycloaliphatic hydrocarbons, these hydrocarbons being themselves, if appropriate, halogenated, such as e.g. toluene, xylene, chlorobenzene, dichlorobenzenes, or nitriles such as acetonitrile, or amides such as N,N-dimethylformamide, or alkanols such as ethanol, this list being non-restrictive. Advantageously the operation is carried out at the boiling point of the solvent employed.

The second stage of the process is carried out advantageously at a temperature of the order of 0° to 100° C. approximately, if appropriate in the presence of an inert solvent. This solvent is generally chosen from those mentioned above in respect of the first stage of the process.

According to a particular embodiment of the invention, hydrocyanic acid is added to the reaction medium, in the form of a solution, or in liquid form, or in gaseous form.

Preferably, however, hydrocyanic acid is formed "in situ" in the reaction medium, by operating according to the method which has already been described in the case of the first process.

Those compounds according to the formula (I) in which $R_0$ denotes the —$CONH_2$ group may be prepared by hydration of the corresponding nitriles by operating according to any usual method for this type of reaction and suitable for this conversion. It is also possible to react a strong acid such as HCl in methanol, in order to hydrolyze it.

Those compounds according to the formula (I) in which $R_0$ denotes the —COOH group may be prepared starting from the amides described above by hydrolysis in an acid medium leading to the acid hydrochloride which is then neutralized with a base to obtain the acid.

Those compounds according to the formula (I) in which $R_0$ denotes a —$COOR_4$ group, in which $R_4$ denotes a lower alkyl radical, may be obtained by esterification of the acid obtained earlier with an alcohol of formula $R_4OH$.

Whatever the process employed, at the end of reaction the compound formed is isolated from the reaction medium by the usual means such as e.g. by distillation of the solvent or by crystallization of the product in the reaction medium, or by filtration, and then, if necessary, it is then purified, e.g. by recrystallization from a suitable solvent, or by chromatography.

The following examples, described without implying a limitation, illustrate the preparation of the compounds according to the invention, as well as their use for combating phytopathogenic fungi. The structures of the compounds described in these examples have been confirmed by nuclear magnetic resonance spectrometry (N.M.R.) and/or by infrared spectrometry.

EXAMPLE 1

Preparation of 2-phenylamino-2-(3-pyridyl)-propanenitrile (compound No. 1), of formula:

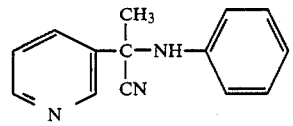

A three-necked round flask arranged under a stirrer and fitted with a thermometer and a reflux condenser is employed. Into the flask are charged in succession acetic acid (50 cc) 3-acetylpyridine (12.1 g) and aniline (9.3 g) and the mixture is kept stirred for 30 minutes at ambient temperature.

Potassium cyanide (8.5 g) dissolved in water (20 cc) is then added.

The mixture is kept at ambient temperature for 20 hours and the precipitate formed is separated by filtration. The solid produced in this way is washed successively with water (200 cc), 10% aqueous solution of $KHCO_3$ (100 cc), water (200 cc) and then pentane.

The crude solid obtained is recrystallized from refluxing ethanol (30 g). 2-Phenylamino-2-(3-pyridyl)-propanenitrile (14 g; 0.063 mole) is obtained in the form of a white solid melting at 156° C.

Yield (calculated on acetylpyridine): 63%.

EXAMPLE 2

Preparation of 2-(4-phenylphenyl)-amino-2-(3-pyridyl)propanenitrile (compound No. 2), of formula:

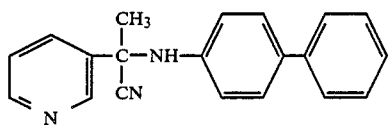

This preparation is carried out according to two successive stages by using the device described in Example 1.

3-Acetylpyridine (6 g), 4-aminodiphenyl (9.3 g) and p-toluenesulphonic acid (0.9 g) are dissolved in toluene (100 cc). The solution is heated to the boiling point of the solvent for 4 hours and the water formed is collected in a Dean-Stark receiver.

After cooling, the solution is washed with water (3×100 cc), dried over sodium sulphate in the presence of animal charcoal and then filtered and evaporated under reduced pressure.

In this way, 3-[1-(4-phenylphenyl)-imino]-ethylpyridine (11.3 g) of formula:

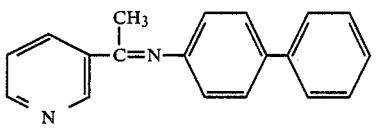

is obtained.

Potassium cyanide (3.9 g) is added to [1-(4-phenylphenyl)-imino]-3-ethylpyridine (11.3 g) in acetic acid (50 cc). The mixture is stirred at ambient temperature for 24 hours. By filtering the reaction mixture a white solid is separated which is washed successively with water (300 cc), a 10% solution (300 cc) of potassium hydrogen carbonate, and water (300 cc). After the product has been dried under reduced pressure, 2-(4-phenylphenyl-amino-2-(3-pyridyl)propanenitrile (7.8 g) is obtained in the form of a white solid melting at 189° C.

Yield (calculated on 3-acetylpyridine): 48%

EXAMPLE 3

The compounds mentioned below were prepared by preceeding according to one or other of the methods described in Examples 1 and 2:

The method employed was that of Example 1 for compound No. 3 to 7, and that of Example 2 for compounds No. 8 to 63 and 72 to 82.

-2-[(methyl)(4-chlorophenyl)amino]-2-(3-pyridyl)acetonitrile, (compound No. 3),

-2-(4-chlorophenyl)amino-2-(3-pyridyl)propanenitrile, (compound No. 4),

-2-(4-fluorophenyl)amino-2-(3-pyridyl)propanenitrile, (compound No. 5),

-2-(2-fluorophenyl)amino-2-(3-pyridyl)propanenitrile, (compound No. 6),

-2-(4-bromophenyl)amino-2-(3-pyridyl)propanenitrile, (compound No. 7),

-2-(3,4-dichlorophenyl)amino-2-(3-pyridyl)propanenitrile, (compound No. 8),

-2-(3-chlorophenyl)amino-2-(3-pyridyl)propanenitrile, (compound No. 9),

-2-(2,4-dichlorophenyl)amino-2-(3-pyridyl)propanenitrile, (compound No. 10),

-2-(4-fluorophenyl)amino-2-phenyl-2-(3-pyridyl)acetonitrile, (compound No. 11),

-2-phenylamino-2-phenyl-2-(3-pyridyl)acetonitrile, (compound No. 12),

-2-(2,4-difluorophenyl)amino-2-(3-pyridyl)propanenitrile, (compound No. 13),

-2-(3-fluorophenyl)amino-2-(3-pyridyl)propanenitrile, (compound No. 14),

-2-(3-chloro-4-fluorophenyl)amino-2-(3-pyridyl)propanenitrile, (compound No. 15), -2-(3-cyanophenyl)-amino-2-(3-pyridyl)propanenitrile, (compound No. 16), -2-(3-bromophenyl)amino-2-(3-pyridyl)propanenitrile, (compound No. 17), -2-(3-methylphenyl)amino-2-(3-pyridyl)propanenitrile, (compound No. 18), -2-(4-chlorophenyl)amino-2-(3-pyridyl)pentanenitrile, (compound No. 19), -2-(3-bromo-4-chlorophenyl)-amino-2-(3-pyridyl)propanenitrile, (compound No. 20), -2-(3,4-dichlorophenyl)amino-2-(3-pyridyl)pentanenitrile, (compound No. 21), -2-(3,4,5-trichlorophenyl)amino-2-(3-pyridyl)propanenitrile, (compound No. 22), -2-(3-chloro-4-fluorophenyl)amino-2-(3-pyridyl)pentanenitrile, (compound No. 23), -2-(3,4-dichlorophenyl)amino-2-(3-pyridyl)-2-phenylacetonitrile, (compound No. 24), -2-(4-chlorophenyl)amino-2-(3-pyridyl)-4-methylpentanenitrile, (compound No. 25), -2-(3,4-dichlorophenyl)amino-2-(3-pyridyl)-4-methylpentanenitrile, (compound No. 26), -2-(3-bromo-4-chlorophenyl)amino-2-(3-pyridyl)-2-phenylacetonitrile, (compound No. 27), -2-(3-chloro-4-fluorophenyl)amino-2-(3-pyridyl)-4-methylpentanenitrile, (compound No. 28), -2-(4-methoxycarbonylphenyl)amino-2-(3-pyridyl)propanenitrile, (compound No. 29), -2-(4-fluorophenyl)amino-2-(3-pyridyl)pentanenitrile, (compound No. 30), -2-(3-methylthiophenyl)amino-2-(3-pyridyl)propanenitrile, (compound No. 31), -2-(4-chlorophenyl)amino-2-(3-pyridyl)butanenitrile, (compound No. 32), -2-(3-chloro-4-fluorophenyl)amino-2-(3-pyridyl)butanenitrile, (compound No. 33), -2-(4-chlorophenyl)amino-2-(3-pyridyl)hexanenitrile, (compound No. 34), -2-(3,4-dichlorophenyl)amino-2-(3-pyridyl)butanenitrile, (compound No. 35), -2-(3-bromophenyl)amino-2-(3-pyridyl)butanenitrile, (compound No. 36), -2-(4-chlorophenyl)amino-2-(3-pyridyl)-3-methylbutanenitrile, (compound No. 37), -2-(4-fluorophenyl)amino-2-(3-pyridyl)-3-methylbutanenitrile, (compound No. 38), -2-(4-fluorophenyl)amino-2-(3-pyridyl)butanenitrile, (compound No. 39), -2-(3-chloro-4-fluorophenyl)amino-2-(3-pyridyl)-3-phenylpropanenitrile, (compound No. 40), -2-(4-trifluoromethylphenyl)amino-2-(3-pyridyl)-butanenitrile, (compound No. 41), -2-(3,4-difluorophenyl)amino-2-(3-pyridyl)butanenitrile, (compound No. 42), -2-phenylamino-2-(3-pyridyl)butanenitrile, (compound No. 43), -2-(3-chloro-4-fluorophenyl)amino-2-(3-pyridyl)-3-methylthiopropanenitrile, (compound No. 44), -2-(4-bromophenyl)amino-2-(3-pyridyl)pentanenitrile, (compound No. 45), -2-(4-bromophenyl)amino-2-(3-pyridyl)butanenitrile, (compound No. 46), -2-(4-chlorophenyl)amino-2-(3-pyridyl)-2-cyclopentylacetonitrile, (compound No. 47), -2-(3,4-difluorophenyl)amino-2-(3-pyridyl)pentanenitrile, (compound No. 48), -2-(3,4-difluorophenyl)amino-2-(3-pyridyl)-3-methylbutanenitrile, (compound No. 49), -2-(4-trifluoromethylphenyl)amino-2-(3-pyridyl)-3-methylbutanenitrile, (compound No. 50), -2-(4-chlorophenyl)amino-2-(5-methyl-3-pyridyl)-butanenitrile, (compound No. 51), -2-(4-chlorophenyl)amino-2-(4-methyl-3-pyridyl)-butanenitrile, compound No. 52), -2-(3-chloro-4-fluorophenyl)amino-2-(4-methyl-3-pyridyl)butanenitrile, (compound No. 53), -2-(4-chlorophenyl)amino-2-(4,5-dimethyl-3-pyridyl)-butanenitrile, (compound No. 54), -2-(3-chloro-4-fluorophenyl)amino-2-(4-ethyl-3-pyridyl)butanenitrile, (compound No. 55), -2-(4-fluorophenyl)amino-2-(4-ethyl-3-pyridyl)-butanenitrile, (compound No. 56), -2-(3,4-dichlorophenyl)amino-2-(4-methyl-3-pyridyl)-propanenitrile, (compound No. 57), -2-(4-chlorophenyl)amino-2-(4-methyl-3-pyridyl)-propanenitrile, (compound No. 58), -2-(4-chlorophenyl)amino-2-(4-methoxy-3-pyridyl)-butanenitrile, (compound No. 59), -2-(4-chlorophenyl)amino-2-(4-methoxy-3-pyridyl)-propanenitrile, (compound No. 60), -2-(3,4-dichlorophenyl)amino-2-(4-methoxy-3-pyridyl)-propanenitrile, (compound No. 61), -2-(3,4-difluorophenyl)amino-2-(4-methyl-3-pyridyl)-butanenitrile, (compound No. 62), -2-(4-bromophenyl)amino-2-(4-methyl-3-pyridyl)-butanenitrile, (compound No. 63), -2-(4-fluorophenyl)amino-2-(4-isopropyl-3-pyridyl)-butanenitrile, (compound No. 72), -2-(4-trifluoromethoxyphenyl)amino-2-(3-pyridyl)-butanenitrile, (compound No. 73), -2-(4-trifluoromethoxyphenyl)amino-2-(3-pyridyl)-propanenitrile, (compound No. 74), -2-(4-trifluoromethoxyphenyl)amino-2-(3-pyridyl)pentanenitrile, (compound No. 75), -2-(4-trifluoromethoxyphenyl)amino-3-methyl-2-(3-pyridyl)butanenitrile, (compound No. 76), -2-(3-trifluoromethoxyphenyl)amino-2-(3-pyridyl)-butanenitrile (compound No. 77), -2-(2-trifluoromethoxyphenyl)amino-2-(3-pyridyl)-butanenitrile (compound No. 78), -2-(3-chloro-4-trifluoromethoxyphenyl)amino-2-(3-pyridyl)butanenitrile (compound No. 79), -2-(3-chloro-4-trifluoromethoxyphenyl)amino-2-(pyridyl)pentanenitrile (compound No. 80), -2-(3-bromo 4-trifluoromethoxyphenyl)amino-2-(3-pyridyl)butanenitrile (compound No. 81), -2-(3-bromo 4-trifluoromethoxyphenyl)amino-2-(3-pyridyl)pentanenitrile (compound No. 82).

EXAMPLE 4

Preparation of the hydrochloride of compound No. 4

A 1.08N solution (18 cc) of HCl in dry ether is added to a solution of 2-(4-chlorophenyl)amino-2-(3-pyridyl)-propanenitrile (5 g) in dry ether (2.5 liters). In this way, after filtering and drying the hydrochloride of compound No. 4 (5.5 g), melting at 120° C., is obtained.

The formula of the compounds mentioned above, their melting point and the yields obtained in their preparation are shown in Table I at the end of the description.

EXAMPLE 5

Preparation of 2-(3,4-dichlorophenyl)-amino-2-(3-pyridyl)propanamide (Compound No. 64)

2-(3,4-dichlorophenyl)amino-2-(3-pyridyl)propanenitrile (compound No. 8) (20 g) and dry methanol (170 cc) are charged into a three-necked round flask.

After the suspension has been cooled to 0.5° C., a stream of gaseous hydrochloric acid is bubbled through slowly to saturation. After return to ambient temperature the reaction mixture is stirred for 16 hours and then diluted with dry ether (150 cc); the solid obtained is filtered off quickly, washed with dry ether (300 cc) and then placed in a 10% aqueous solution of potassium hydrogen carbonate. After filtering, washing with distilled water and ethanol and drying under vacuum, 2-(3,4-dichlorophenyl)aminopropanamide (19.6 g) is obtained in the form of a white solid melting at 175° C. (yield 92%).

EXAMPLE 6

Preparation of 2-(3,4-dichlorophenyl)-amino-2-(3-pyridyl)propanoic acid (compound No. 65)

2-(3,4-dichlorophenyl)amino-2-(3-pyridyl)propanamide (compound No. 64) (19.2 g) and 6N hydrochloric acid (190° cc) are charged into a three-necked round flask and heated under reflux for 7 hours. A precipitate is then formed which is filtered off and treated with water (800 cc) and concentrated ammonia solution (25 cc).

The ammonium salt solution heated to 50° C. is next filtered and then treated with glacial acetic acid (25 cc).

After being filtered off, the solid is washed with water and then dried under vacuum. 2-(3,4-dichlorophenyl)amino-2-(3-pyridyl)propanoic acid (13.2 g) is obtained in the form of a solid melting at 190° C.

EXAMPLE 7

Preparation of methyl 2-(3,4-dichlorophenyl)amino-2-(3-pyridyl)propanoate (compound No. 66)

2-(3,4-dichlorophenyl)amino-2-(3-pyridyl)propanoic acid (compound No. 64) (4.8 g) in dry methanol (25 cc) is charged into a three-necked round flask. After cooling to minus 10° C., sulphinyl chloride (1.3 cc) is added in a single portion, and the mixture is heated slowly to reflux.

After 3 hours the temperature is reduced again to minus 10° C., and sulphinyl chloride (1.3 cc) is again added.

After 5 hours' heating under reflux the reaction mixture is evaporated down under reduced pressure and the crude product is then treated in succession with ether (50 cc), distilled water (50 cc), and potassium hydrogen carbonate (5 g).

After separation, the organic phase is dried over sodium sulphate and then evaporated down. The oily residue is purified by chromatography on a silica column (eluent: ether). Methyl 2-(3,4-dichlorophenyl)amino-2-(3-pyridyl)propanoate (3.5 g), light yellow in colour, is obtained.

Yield 72%.

EXAMPLE 8

By proceeding according to the method described in Example 7 above, the following compounds have been prepared from appropriate starting materials.

No. 67: methyl 2-(4-chlorophenylamino-2-(3-pyridyl)propanoate, melting at 94° C.

No. 68: methyl 2-(4-chlorophenyl)amino-2-(3-pyridyl)butanoate, melting at 154° C.

No. 69: methyl 2-(3,4-dichlorophenyl)amino-2-(3-pyridyl)butanoate, melting at 112° C.

No. 70: methyl 2-(3-bromo-4-chlorophenyl)amino-2-(3-pyridyl)butanoate, melting at 110° C.

No. 71: methyl 2-(3,4-dichlorophenyl)amino-2-(3-pyridyl)pentanoate, in the form of a yellow oil.

Examples No. 9 to 13 below illustrate the biological activity of the compounds according to the invention.

EXAMPLE 9

Greenhouse test on barley mildew-curative treatment

An aqueous suspension of the active ingredient to be tested having the following composition is prepared by fine grinding:

| | |
|---|---|
| active ingredient to be tested . . . | 40 mg |
| Tween 80 (surface-active agent consisting of a monolaurate of a condensate of ethylene oxide derived from sorbitan) . . . | 0.4 cc |
| water . . . | 40 cc |

This aqueous suspension is then diluted with water to obtain the required concentration.

Barley plants (*Hordeum vulgare*), of Berac variety, are grown in pots. When these plants are five days old they are contaminated by being dusted with spores of barley mildew (*Erysiphe graminis*) and then kept in a greenhouse at 22° C. plus or minus 2° C. under 70 to 80% relative humidity.

Two days after contamination, when the foliage is invaded by mildew the plants are treated by spraying on each of them a suspension (8 cc) of the active ingredient in distilled water containing 0.02% by weight of Tween 80, at the required concentration.

Each concentration of the active ingredient is repeated three times. The control plants are treated in the same manner but without active ingredient.

The treated plants are then placed again in a greenhouse, under the temperature and humidity conditions described above.

Ten days after the treatment with the suspension of the active ingredient, the percentage inhibition of the development of the fungus is evaluated by comparison with the untreated control.

Under these conditions, it was found that, at a concentration of 500 mg/liter, the percentage inhibition of the development of the fungus was respectively:

at least 90% for the compounds Nos. 4, 10, 15, 17, 19, 20, 21, 25, 26, 27, 28, 30, 32, 33, 34, 35, 36, 37, 38, 39, 42, 43, 73, 74, 75, 76, at least 70% (but less than 90%) for the compounds Nos. 1, 2, 3, 5, 6, 7, 8, 9, 11, 12, 13, 14, 18, 23, 29, 40, 44, 51, 56, at least 20% (but less than 70%) for the compounds Nos. 41, 47, 48, 77, 78.

Under these conditions, it was found that, at a concentration of 1g/liter, the percentage inhibition of the fungus was at least 90% for the compounds Nos. 79, 80, 81, 82.

EXAMPLE 10

Antifungal activity towards Botrytis cinerea in the tomato:

Tomatoes grown in a greenhouse (Marmande variety) 60 to 75 days old are treated by spraying with aqueous suspensions of the same composition as that described in the preceding Example and at various concentrations of active ingredient. The test is repeated twice with each concentration.

After 24 hours, the leaves are cut off and placed in two Petri dishes (11 cm diameter) the bottom of which has first been lined with a disc of moist filter paper (5 leaflets per dish).

The inoculum is then added with the aid of a syringe by depositing drops (3 drops per leaflet) of a spore suspension. This suspension of spores of *Botrytis cinerea* has been obtained from a 15-day culture, then placed in suspension in a nutrient solution (80,000 units/cc). The assessment is carried out approximately 4 days after the contamination by comparison with an untreated control. The percentage protection relative to the untreated control is thus evaluated.

Under these conditions, it is seen that, at a concentration of 1,000 mg/liter, the percentage protection was respectfully:

at least 95% for the compounds Nos. 4, 5, 7, 8, 9, 14, 15, 19, 23, 29, 30, 32, 33, 34, 35, 37, 42, 43, 44, 45, 48, 49, 55, 56, 57, 58, 59, 61, 62, 63, 66, 73, at least 80% (but less than 95%) for the compounds Nos. 17, 25, 28, 51, 60, at least 50% (but less than 80%) for the compounds Nos. 16, 18, 20, 36, 38, 39, 41, 46, 50, 52, 65, 79, at least 20%, (but less than 50%) for the compounds Nos. 24, 26, 40, 53 and 54.

EXAMPLE 11

Antifungal activity towards cercosporiosis in sugarbeet (*Cercospora Beticola*)

Sugarbeets (*Beta vulgaris*) Monostar variety are grown in a greenhouse in plastic pots containing a mixture of sand and river peat (1/1). After 12 days, when the plantlets are at the 2-leaf stage, 5 to 7 cm high, they are treated by spraying with aqueous suspensions of the same composition as that described in the preceding Example, at various concentrations of active ingredient. Each pot receives approximately 5 cc of preparation, corresponding substantially to a dose rate of 1,000 liters/ha. Each concentration of active ingredient corresponds to three pots.

The inoculum is then added with the aid of a sprayer, so that each pot receives approximately 5 cc of this suspension. After this contamination, the plants are incubated, first for 2 days at 26° C., in a saturated humidity atmosphere and in darkness, then for approximately 12 days under normal greenhouse conditions (22±2° C. and 60 to 80% humidity).

The assessment is carried out fourteen days after the contamination and the percentage protection relative to the untreated control is thus evaluated.

Under these conditions, it is seen that, at a concentration of 1,000 mg/liter, the percentage protection was respectively:

at least 95% for the compounds Nos. 19, 21, 23, 25, 26, 28, 30, 32, 33, 37, 42,
at least 80% (but less than 95%) for the compounds Nos. 35, 36, 46,
at least 50% (but less than 80%) for the compounds Nos. 20, 29.

EXAMPLE 12

Test in vivo on "Puccinia recondita" responsible for wheat rust.

Wheat, sown in pots in loam, is treated at the stage where it is 10 cm in height by spraying it with aqueous emulsions (referred to as spray mixtures) of the same compositions as that described in Example 4, and at various concentrations of the compound to be tested. The trial is repeated twice with each concentration.

After 48 hours, an aqueous suspension of spores (50,000 sp/cc) is sprayed onto the wheat; this suspension has been obtained from contaminated plants. The wheat is then placed for 48 hours in an incubation cell at approximately 18° C. and 100% relative humidity.

After these 2 days, the relative humidity is lowered to 60%. The condition of the plants is verified between the 11th and 15th day after contamination by comparison with the untreated control.

Under these conditions, the following results are observed:

at a dose of 1 g/l the percentage of protection was respectively:
at least 90% for the compounds Nos. 73, 74, 75, 76, 79, 81.
at least 50% for the compound No. 76.

EXAMPLE 13

Antifungal activity towards rice blast (*Piricularia oryzae*)

Rice plants (*Orysa sativa*) Marchetti rosa variety are grown in a greenhouse in plastic pots containing a mixture of sand and river peat (1/1). After 10 days, when the plantlets are at the 2-leaf stage, 5 to 7 cm high, they are treated by spraying with aqueous suspension of the same composition as that described in the preceding Example, at various concentration of active ingredient.

Each pot receives approximately a dose of preparation, corresponding substantially to a dose rate of 1,000 l/ha. Each concentration of active ingredient corresponds to two pots.

One day after the treatment, the inoculum is then added with the aid of a sprayer, so that each pot receives approximately 5 cc of this suspension. After this contamination, the plants are incubated, first for 1 day at 25° C., in a saturated humidity atmosphere and in 12/12 photoperiod system, then for approximately 6 days under normal greenhouse conditions (25° C. and 90 to 95% humidity).

The assessment is carried out seven days after the contamination and the percentage protection relative to the untreated control is thus evaluated.

Under these conditions, it is seen that, at a concentration of 1,000 mg/liter, the percentage protection was respectively:

at least 95% for the compounds Nos. 73, 79, 81
at least 50% for the compound No. 76
at least 25% for the compound No. 80.

These results illustrate the good antifungal activity of the compounds according to the invention.

The compounds according to the invention are of great interest on account of their activity towards sclerotiniaceae, particularly towards Botrytis and as a result may be applied to crops such as cereals (e.g. barley), rice, sugar, sugar beet, vine, some tropical crops such as groundnut and banana, market garden (e.g. tomato) and floral crops and in arboriculture (e.g. fruit-trees).

For their use in practice, the compounds according to the invention are rarely employed alone. Most frequently these compounds form part of compositions. These compositions, which can be employed as antifungal agents, contain as an active ingredient a compound according to the invention such as described earlier in combination with solid or liquid supports which are agriculturally acceptable and surface-active agents which are also agriculturally acceptable. In particular, the usual inert supports and the usual surface-active agents can be employed. These compositions also form part of the invention.

These compositions may also contain all kinds of other ingredients such as, e.g., protective colloids, adhesives, thickeners, thixotropic agents, penetrating agents, stabilizers, sequestering agents, and the like, as well as other known active ingredients with pesticidal properties (particularly fungicides). More generally, the compounds employed in the invention may be combined with all the solid or liquid additives corresponding to the usual techniques employed in formulation. In a general manner, the compositions according to the invention usually contain from 0.001 to 95% approximately (by weight) of one or more active ingredients according to the invention, from 1 to 95% approximately of one or more solid or liquid supports and, if appropriate, from 0.1 to 20% approximately of one or more surface-active agents.

In accordance with what has already been said, the compounds employed in the invention are generally combined with supports and, if appropriate, surface-active agents.

The term "support", in the present description, refers to an organic or inorganic substance, natural or synthetic, with which the active ingredient is combined to facilitate its application to the plant, seeds or the soil. This support is therefore generally inert and it must be agriculturally acceptable, particularly on the treated plant. The support may be solid (clays, natural or synthetic silicates, silica, resins, waxes, solid fertilizers, and the like) or liquid (water; alcohols, particularly butanol; esters, particularly methyl glycol acetate; ketones, particularly cyclohexanone and isophorone; petroleum fractions; aromatic hydrocarbons, particularly xylenes, or paraffinic hydrocarbons, aliphatic chlorinated hydrocarbons, particularly trichloroethane, or aromatic chlorinated hydrocarbons, particularly chlorobenzenes; water-soluble solvents such as dimethylformamide, dimethyl sulphoxide, N-methylpyrrolidone; liquefied gases, and the like).

The surface-active agent may be an emulsifying, dispersing or wetting agent of an ionic or nonionic type or a mixture of such surface-active agents. For example, mention can be made of salts of polyacrylic acids, salts of lignosulphonic acids, salts of phenolsulphonic or naphthalenesulphonic acids, polycondensates of ethylene oxide with fatty alcohols or fatty acids or fatty amines, substituted phenols (particularly alkylphenols or arylphenols), salts of sulphosuccinic acid esters, taurine derivatives (particularly alkyltaurates), phosphoric esters of alcohols or of condensates of ethylene oxide with phenols, esters of fatty acids and polyols, derivatives of the preceding compounds containing sulphate, sulphonate and phosphate functions. The presence of at least one surface-active agent is generally essential when the active ingredient and/or the inert support are insoluble in water and when the vector agent for application is water.

For their application, the compounds of formula (I) are therefore generally in the form of compositions; these compositions according to the invention are themselves in diverse forms, solid or liquid.

As forms of solid compositions mention can be made of powders for powdering (with a concentration of compound of formula (I) which can go up to 100%) and granulates, particularly those produced by extrusion, compacting, impregnation of a granular support, granulation from a powder (the content of compound of formula (I) in these granulates being between 0.5 and 80% in these latter cases).

As forms of liquid compositions or those intended to form liquid compositions during the application, mention can be made of solutions, in particular emulsifiable concentrates, emulsions, flowables, aerosols, wettable powders (or powder for spraying), dry flowables and pastes.

The emulsifiable or soluble concentrates also contain in most cases 10 to 80% of active ingredient; while the emulsions or solutions which are ready for use contain, in their case, 0.01 to 20% of active ingredient. In addition to the solvent, the emulsifiable concentrates may contain, when necessary, 2 to 20% of suitable additives, such as stabilizers, surface-active agents, penetrating agents, corrosion inhibitors, colorants or adhesives.

From these concentrates it is possible to produce, by dilution with water, emulsions of any desired concentration which are particularly suitable for application to plants. As an example, here is the composition of some emulsifiable concentrates:

| active ingredient | 250 g |
| condensate of ethylene oxide with alkylphenol | 30 g |
| calcium alkylarylsulphonate | 50 g |
| petroleum distillation cut, distilling between 160 and 185° C. | 670 g |

Another formula:

| active ingredient | 350 g |
| condensate of ethylene oxide with castor oil | 60 g |
| sodium alkylarylsulphonate | 40 g |
| cyclohexanone | 150 g |
| xylene | 400 g |

Another formula:

| active ingredient | 400 g |
| condensate of ethylene oxide with alkylphenol | 100 g |
| ethylene glycol methyl ether | 250 g |
| aromatic petroleum cut distilling between 160–185° C. | 250 g |

Another formula:

| active ingredient | 400 g |
| condensate of ethylene oxide with tristyrylphenol phosphate | 50 g |
| condensate of ethylene oxide with alkylphenol phosphate | 65 g |
| sodium alkylbenzenesulphonate | 35 g |
| cyclohexanone | 300 g |
| aromatic petroleum cut distilling between 160–185° C. | 150 g |

Another formula:

| active ingredient | 400 g/liter |
| alkali metal dodecylbenzenesulphonate | 24 g/liter |
| nonylphenol condensed with 10 molecules of ethylene oxide | 16 g/liter |
| cyclohexanone | 200 g/liter |
| aromatic solvent q.s. | 1 liter. |

According to another formula for emulsifiable concentrate, use is made of:

| active ingredient | 250 g |
| epoxydized vegetable oil | 25 g |
| mixture of alkylarylsulphonate and polyglycol ether and fatty alcohols | 100 g |
| dimethylformamide | 50 g |
| xylene | 575 g |

The flowables, which can be applied by spraying, are prepared so as to produce a stable fluid product which does not settle (fine grinding) and they usually contain from 10 to 75% of active ingredient, from 0.5 to 15% of surface-active agents, from 0.1 to 10% of thixotropic agents, from 0 to 10% of suitable additives, such as antifoams, corrosion inhibitors, stabilizers, penetrating agents and adhesives and, as a support, water or an organic liquid in which the active ingredient is poorly soluble or insoluble: some organic substances or inorganic salts may be dissolved in the support to help to prevent settling or as antifreezes for water.

As an example, here is a composition of a flowable:

| active ingredient | 500 g |
| condensate of ethylene oxide with tristyrylphenol phosphate | 50 g |
| condensate of ethylene oxide with alkylphenol | 50 g |
| sodium polycarboxylate | 20 g |
| ethylene glycol | 50 g |
| organopolysiloxane oil (antifoam) | 1 g |
| polysaccharide | 1.5 g |
| water | 316.5 g |

The wettable powders (or spraying powder) are usually prepared so that they contain 20 to 95% of active ingredient, and they usually contain, in addition to the solid support, from 0 to 5% of a wetting agent, from 3 to 10% of a dispersing agent and, when required, from 0 to 10% of one or more stabilizers and/or other additives, such as penetrating agents, adhesives, or anti-caking agents, colorants, and the like.

As an example, here are various compositions of wettable powders:

| | |
|---|---|
| active ingredient (compound No. 4) | 50% |
| calcium lignosulphonate (deflocculant) | 5% |
| isopropylnaphthalene sulphonate (anionic wetting agent) | 1% |
| anti-caking silica | 5% |
| kaolin (filler) | 39% |

Another example of an 80% wettable powder is given below:

| | |
|---|---|
| active ingredient (compound No. 7) | 80% |
| sodium alkylnaphthalenesulphonate | 2% |
| sodium lignosulphonate | 2% |
| anti-caking silica | 3% |
| kaolin | 13% |

Another example of a wettable powder is given below:

| | |
|---|---|
| active ingredient (compound No. 14) | 50% |
| sodium alkylnaphthalenesulphonate | 2% |
| low-viscosity methylcellulose | 2% |
| diatomaceous earth | 46% |

Another example of a wettable powder is given below:

| | |
|---|---|
| active ingredient (compound No. 19) | 90% |
| sodium dioctylsulphosuccinate | 0.2% |
| synthetic silica | 9.8% |

Another composition of a 40% powder for spraying uses the following components:

| | |
|---|---|
| active ingredient (compound No. 33) | 400 g |
| sodium lignosulphonate | 50 g |
| sodium dibutylnaphthalenesulphonate | 10 g |
| silica | 540 g |

Another composition of a 25% powder for spraying uses the following components:

| | |
|---|---|
| active ingredient (compound No. 37) | 250 g |
| isooctylphenoxy-polyoxyethylene-ethanol | 25 g |
| equal weight mixture of champagne chalk and hydroxyethylcellulose | 17 g |
| sodium aluminosilicate | 543 g |
| kieselguhr | 165 g |

Another composition of a 10% powder for spraying uses the following components:

| | |
|---|---|
| active ingredient (compound No. 42) | 100 g |
| mixture of sodium salts of sulphates of saturated fatty acids | 30 g |
| condensation product of naphthalene sulphonic acid and formaldehyde | 50 g |
| kaolin | 820 g |

To obtain these powders for spraying or wettable powders, the active ingredients are intimately mixed in suitable mixers with additional substances where the molten active ingredient is impregnated on the porous filler and they are ground by means of mills or other suitable grinders. This produces powders for spraying whose wettability and suspendability are advantageous; they can be suspended using water at any required concentration and this suspension can be used very advantageously in particular for application to plant foliage.

The "autodispersible" granulates ("dry flowables"; more precisely these are granulates which are readily dispersible in water) have a composition which is substantially close to that of the wettable powders. They may be prepared by granulation of formulations described for the wettable powders, either by a wet route (contacting finely divided active ingredient with the inert filler and with a little water, e.g. 1 to 20%, or aqueous solution of dispersant or of binder, followed by drying and screening), or by a dry route (compacting followed by grinding and screening).

As an example, here is a formulation of a dry flowable:

| | |
|---|---|
| active ingredient | 800 g |
| sodium alkylnaphthalenesulphonate | 20 g |
| sodium methylenebisnaphthalenesulphonate | 80 g |
| kaolin | 100 g |

In place of wettable powders it is possible to produce pastes. The conditions and methods for producing and using these pastes are similar to those for wettable powders for spraying.

As already stated, the aqueous dispersions and emulsions, e.g. compositions obtained by diluting with water a wettable powder or an emulsifiable concentrate according to the invention, are included in the general range of the compositions which may be employed in the present invention. The emulsions may be of the water-in-oil or oil-in-water type and they may have a thick consistency such as that of a "mayonnaise".

All these aqueous dispersions or emulsions or spraying mixtures can be applied to the crops to be weeded by any suitable means, mainly by spraying, at doses which are generally of the order of 100 to 1,200 liters of spraying mixture per hectare.

The granulates intended to be scattered on the ground are usually prepared so that they have dimensions of between 0.1 and 2 mm and can be produced by agglomeration or impregnation. Preferably, the granulates contain 1 to 25% of active ingredient and 0 to 10% of additives such as stabilizers, slow-release modifying agents, binders and solvents.

According to an example of granulate composition, the following components are employed:

| | |
|---|---|
| active ingredient | 50 g |
| propylene glycol | 25 g |
| boiled linseed oil | 50 g |
| clay (particle size distribution: 0.3 to 0.8 mm) | 910 g |

The invention also relates to a process for treating plants against phytopathogenic fungi.

This process consists in applying to these plants an effective quantify of a composition containing as active ingredient a compound according to the formula (I). "Effective quantity" is understood to means a quantity sufficient to permit the control and the destruction of fungi present on these plants. The usage doses can nevertheless vary within wide limits according to the fungus to be combated, the type of crop, weather conditions, and depending on the compound employed.

In practice, the active ingredients according to the invention are advantageously applied at dose rates ranging from 10 g/ha to 2,000 g/ha approximately, use being made for this purpose of spraying mixtures containing the active ingredient at the required concentration and applied at a rate of 10 liters/ha to 3,000 liters/ha.

Preferred compounds may be chosen from amongst compounds Nos. 4, 7, 8, 19, 21, 23, 32, 33, 35, 37, 42, 44, 55.

Comparative tests

In order to demonstrate the efficacy of the present invention in view of U.S. Pat. No. 3,313,683 and Chem. Abs. 68 No. 68,602 g (1968) discussed at page 4 of the specification, the following compounds were tested:
-2-(3-pyridyl)2-dimethylamino acetonitrile corresponding to the basic form of the compound described in U.S. Pat. No. 3,313,685, Column 3, Lines 35-36 (compound No. 83).
-2-(3-pyridyl)2-dimethylamino acetonitrile dihydrochloride corresponding to the compound described in U.S. Pat. No. 3,313,685, Column 3, Lines 35-36 (compound No. 84).
-2-(4-chlorophenyl)amino 2-(2-pyridyl)propanenitrile which is quite similar to the compound described in Chem. Abs. 68, 68,602 g (1968) (compound No. 85).

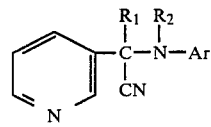

The compounds 83, 84 and 85 were tested according to the methods described in examples 9, 10, 11, 12, 13 and exhibited no activity at a dose of 1 g/l.

TABLE I

Compounds corresponding to the formula A

| Compound No. | $R_1$ | $R_2$ | Ar | Melting point (°C.) | Yield % |
|---|---|---|---|---|---|
| 1 | $CH_3$ | H | $C_6H_5$ | 156 | 63 |
| 2 | $CH_3$ | H | p-$C_6H_5$—$C_6H_4$ | 189 | 48 |
| 3 | H | $CH_3$ | p-Cl—$C_6H_4$ | 50 | 39 |
| 4 | $CH_3$ | H | p-Cl—$C_6H_4$ | 160 | 21 |
| 5 | $CH_3$ | H | p-F—$C_6H_4$ | 160 | 29 |
| 6 | $CH_3$ | H | o-F—$C_6H_4$ | 140 | 10 |
| 7 | $CH_3$ | H | p-Br—$C_6H_4$ | 157 | 24 |
| 8 | $CH_3$ | H | m,p-$Cl_2$—$C_6H_3$ | 170 | 36 |
| 9 | $CH_3$ | H | m-Cl—$C_6H_4$ | 130 | 22 |
| 10 | $CH_3$ | H | o,p-$Cl_2$—$C_6H_3$ | 168 | 25 |
| 11 | $C_6H_5$ | H | p-F—$C_6H_4$ | 125 | 30 |
| 12 | $C_6H_5$ | H | $C_6H_5$ | 150 | 25 |
| 13 | $CH_3$ | H | o,p-$F_2$—$C_6H_3$ | 133 | 50 |
| 14 | $CH_3$ | H | m-F—$C_6H_4$ | 124 | 41 |
| 15 | $CH_3$ | H | m-Cl,p-F—$C_6H_3$ | 126 | 29 |
| 16 | —$CH_3$ | H | m-CN—$C_6H_4$ | 164 | 38 |
| 17 | —$CH_3$ | H | m-Br—$C_6H_4$ | 131 | 43 |
| 18 | —$CH_3$ | H | m-$CH_3$—$C_6H_4$ | 144 | 51 |
| 19 | —$(CH_2)_2CH_3$ | H | p-Cl—$C_6H_4$ | 132 | 21 |
| 20 | —$CH_3$ | H | m-Br,p-Cl—$C_6H_3$ | 173 | 42 |
| 21 | —$(CH_2)_2CH_3$ | H | m,p-$Cl_2C_6H_3$ | 160 | 27 |
| 22 | —$CH_3$ | H | 3,4,5$Cl_3$—$C_6H_2$ | 149 | 10 |
| 23 | —$(CH_2)_2CH_3$ | H | m-Cl,p-F—$C_6H_3$ | 119 | 14 |
| 24 | —$C_6H_5$ | H | m,p-$Cl_2$—$C_6H_3$ | 180 | 24 |
| 25 | —$CH_2$—$CH(CH_3)_2$ | H | p-Cl—$C_6H_4$ | 125 | 30 |
| 26 | —$CH_2$—$CH(CH_3)_2$ | H | m.p-$Cl_2$—$C_6H_3$ | 132 | 17 |
| 27 | —$C_6H_5$ | H | m-Br,p-Cl—$C_6H_3$ | 168 | 42 |
| 28 | —$CH_2$—$CH(CH_3)_2$ | H | m-Cl,p-F—$C_6H_3$ | 113 | 40 |
| 29 | —$CH_3$ | H | p-(COOCH)$_3$—$C_6H_4$ | 174 | 31 |
| 30 | —$(CH_2)_2CH_3$ | H | p-F—$C_6H_4$ | 116 | 37 |
| 31 | —$CH_3$ | H | m-$SCH_3$—$C_6H_4$ | 121 | 66 |
| 32 | —$C_2H_5$ | H | p-Cl—$C_6H_4$ | 161 | 49 |
| 33 | —$C_2H_5$ | H | m-Cl-p-F—$C_6H_3$ | 123 | 18 |
| 34 | —$(CH_2)_3$—$CH_3$ | H | p-Cl—$C_6H_4$ | 114 | 11 |
| 35 | —$C_2H_5$ | H | m,p-$Cl_2$—$C_6H_3$ | 142 | 61 |
| 36 | —$C_2H_5$ | H | m-Br—$C_6H_4$ | 132 | 11 |
| 37 | —$CH(CH_3)_2$ | H | p-Cl—$C_6H_4$ | 157 | 21 |
| 38 | —$CH(CH_3)_2$ | H | p-F—$C_6H_4$ | 137 | 43 |

TABLE I-continued

| | | | | | |
|---|---|---|---|---|---|
| 39 | $-C_2H_5$ | H | p-F—$C_6H_4$ | 117 | 19 |
| 40 | $-CH_2-C_6H_5$ | H | m-Cl,p-F—$C_6H_3$ | 160 | 55 |
| 41 | $-C_2H_5$ | H | p-CF$_3$—$C_6H_4$ | 162 | 48 |
| 42 | $-C_2H_5$ | H | m,p-F$_2$—$C_6H_3$ | 108 | 51 |
| 43 | $-C_2H_5$ | H | $C_6H_5$ | 158 | 75 |
| 44 | $-CH_2-S-CH_3$ | H | m-Cl,p-F—$C_6H_3$ | 119 | 24 |
| 45 | $-(CH_2)_2CH_3$ | H | p-Br—$C_6H_4$ | 146 | 51 |
| 46 | $-C_2H_5$ | H | p-Br—$C_6H_4$ | 176 | 62 |
| 47 | cyclopentyle | H | p-Cl—$C_6H_4$ | 163 | 156 |
| 48 | $-(CH_2)_2CH_3$ | H | m,p-F$_2$—$C_6H_3$ | 110 | 57 |
| 49 | $-CH(CH_3)_2$ | H | m,p-F$_2$—$C_6H_3$ | 160 | 28 |
| 50 | $-CH(CH_3)_2$ | H | p-CF$_3$—$C_6H_4$ | 143 | 19 |

Compounds corresponding to the formula B

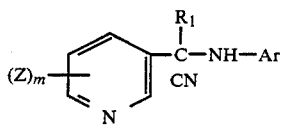

| Compound No. | (Z)$_m$ pyridine | $R_1$ | Ar | Melting point (°C.) | Yield % |
|---|---|---|---|---|---|
| 51 | 5-CH$_3$ pyridin-3-yl | $-C_2H_5$ | p-Cl—$C_6H_4$ | 147 | 50 |
| 52 | 4-CH$_3$ pyridin-3-yl | $-C_2H_5$ | p-Cl—$C_6H_4$ | 146 | 37 |
| 53 | 4-CH$_3$ pyridin-3-yl | $-C_2H_5$ | m-Cl—pF—$C_6H_3$ | 155 | 44 |
| 54 | 3,4-(CH$_3$)$_2$ pyridin-5-yl | $-C_2H_5$ | p-Cl—$C_6H_4$ | 123 | 22 |
| 55 | 4-C$_2$H$_5$ pyridin-3-yl | $-C_2H_5$ | m-Cl,-pF—$C_6H_3$ | 148 | 47 |
| 56 | 4-C$_2$H$_5$ pyridin-3-yl | $-C_2H_5$ | -p-F—$C_6H_5$H | 117 | 14 |
| 57 | 4-CH$_3$ pyridin-3-yl | CH$_3$ | m,p-Cl$_2$—$C_6H_3$ | 156 | 41 |
| 58 | 4-CH$_3$ pyridin-3-yl | CH$_3$ | p-Cl—$C_6H_4$ | 180 | 69 |

TABLE I-continued

| No. | (pyridine substituent) | R | Ar | Melting point (°C.) | Yield % |
|---|---|---|---|---|---|
| 59 | 4-OCH₃-pyridin-3-yl | —C₂H₅ | p-Cl—C₆H₄ | 89 | 32 |
| 60 | 4-OCH₃-pyridin-3-yl | CH₃ | p-Cl—C₆H₄ | 171 | 25 |
| 61 | 4-OCH₃-pyridin-3-yl | CH₃ | m,p-Cl₂—C₆H₃ | 145 | 21 |
| 62 | 4-CH₃-pyridin-3-yl | —C₂H₅ | m,p-F₂—C₆H₃ | 138 | 42 |
| 63 | 4-CH₃-pyridin-3-yl | —C₂H₅ | p-Br—C₆H₄ | 155 | 43 |
| 72 | 4-iPr-pyridin-3-yl | —C₂H₅ | p-F—C₆H₄ | 172 | 7 |

Compounds corresponding to the formula A

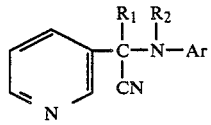

| Compound No. | R₁ | R₂ | Ar | Melting point (°C.) | Yield % |
|---|---|---|---|---|---|
| 73 | C₂H₅ | H | p-O—CF₃—C₆H₄ | 116 | 69 |
| 74 | CH₃ | H | p-O—CF₃—C₆H₄ | 138 | 77 |
| 75 | C₃H₇ | H | p-O—CF₃—C₆H₄ | 117 | 38 |
| 76 | i-C₃H₇ | H | p-O—CF₃—C₆H₄ | 134 | 15 |
| 77 | C₂H₅ | H | m-O—CF₃—C₆H₄ | 113 | 56 |
| 78 | C₂H₅ | H | o-O—CF₃—C₆H₄ | oil | 25 |
| 79 | C₂H₅ | H | m-Cl,p-O—CF₃—C₆H₄ | 108 | 15 |
| 80 | C₃H₇ | H | m-Cl,p-O—CF₃—C₆H₄ | 134 | 58 |
| 81 | C₂H₅ | H | m-Br,p-O—CF₃—C₆H₄ | 117 | 67 |
| 82 | C₃H₇ | H | m-Br,p-O—CF₃—C₆H₄ | 133 | 44 |

What is claimed is:

1. A compound of the general formula (I):

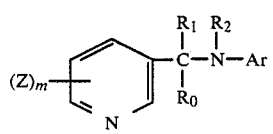

in which $R_0$ denotes a radical chosen from the radicals —CN, —COOH, CONH₂ and the radical —COOR₄ in which R₄ denotes a lower alkyl radical, $R_1$ denotes the hydrogen atom, lower alkyl radical, which is unsubstituted or substituted with halogen, hydroxy, lower alkoxy or lower alkylthio; lower cycloalkyl radical, which is unsubstituted or substituted with halogen, hydroxy, lower alkoxy or lower alkylthio; phenyl radical, which is unsubstituted or substituted with halogen or lower alkyl;

aralkyl radical, which is unsubstituted or substituted with halogen;

R$_2$ denotes the hydrogen atom or a lower alkyl radical which is unsubstituted or substituted with halogen, hydroxy, lower alkoxy or lower alkylthio, provided that R$_1$ and R$_2$ do not simultaneously denote the hydrogen atom;

Z denotes a halogen atom or a lower alkyl radical, lower alkoxy radical or lower alkylthio radical;

m is equal to 0, 1, 2, 3 or 4 it being understood that when m is greater than 1 the substituents Z may be either identical or different;

Ar denotes a phenyl radical which is unsubstituted or substituted with halogen, lower alkyl, lower cycloalkyl, lower alkenyl, lower alkylthio, cyano, nitro, hydroxy, carboxy, lower alkoxy carbonyl, carbamoyl, N-alkyl carbamoyl, N,N-dialkyl carbamoyl, N-piperidinyl carbonyl, N-pyrolidinyl carbonyl, N-azepinyl carbonyl, N-morpholinyl carbonyl, N-1-piperazinyl carbonyl or phenyl, and salts obtained by reaction of the compound according to the Formula (I) with a suitable acid or base, as well as stereoisomeric forms of this compound, alone or intermixed.

2. Compound according to claim 1, of the formula (II):

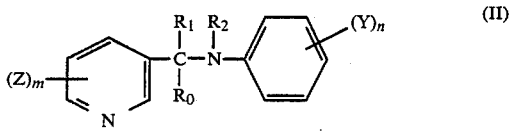

in which:

R$_0$ denotes the —CN group or a —COOR$_4$ group in which R$_4$ has the same meaning as in claim 1, R$_1$ denotes a lower alkyl radical or lower cycloalkyl radical, R$_2$ denotes the hydrogen atom or the methyl radical, Z denotes an alkyl or alkoxy radical containing from 1 to 3 carbon atoms, m is equal to 0, 1 or 2, it being understood that when m is equal to 2, the substituents Z may be either identical or different, Y denotes a halogen atom, an alkyl radical containing from 1 to 3 carbon atoms, a haloalkyl radical containing from 1 to 3 carbon atoms, an alkoxy radical containing from 1 to 3 carbon atoms, an halogen substituted alkoxy containing from 1 to 3 carbon atoms, alkylthio radical containing from 1 to 3 carbon atoms, an halogen substituted alkylthio containing from 1 to 3 carbon atoms, a lower alkoxycarbonyl, phenyl, or lower cycloalkyl radical, n is equal to 0, 1, 2, 3 or 4, it being understood that when n is greater than 1 the substituents Y may be either identical or different, or agriculturally acceptable salts of these compounds.

3. Compound according to claim 2, wherein in the formula (II):

R$_0$ has the same meaning as in claim 2,

R$_1$ denotes an alkyl radical containing from 1 to 5 carbon atoms,

R$_2$ denotes the hydrogen atom,

Z denotes a methyl, ethyl or methoxy radical, m is equal to 0, 1 or 2,

Y denotes a fluorine, chlorine or bromine atom or an halogen substituted alkoxy or aklylthio radical, n is equal to 1 or 2, it being understood that, when m is equal to 2, the substituents Z may be either identical or different, and that when n is equal to 2, the substituents Y may be either identical or different, or agriculturally acceptable salts of these compounds.

4. Compound according to claim 3, wherein, in the formula (II):

n is equal to 1, 2, 3 or 4 on the condition that at least one Y is an halogen substituted alkoxy or alkylthio radical.

5. The compound according to claim 1 which is 2-(4-chlorophenyl)amino-2-(3-pyridyl)butanenitrile.

6. The compound according to claim 1 which is 2-(3-chloro-4-fluorophenyl)amino-2-(3-pyridyl)butanenitrile.

7. The compound according to claim 1 which is 2-(3,4-dichlorophenyl)amino-2-(3-pyridyl)butanenitrile.

8. The compound according to claim 1 which is 2-(4-chlorophenyl)amino-2-(3-pyridyl)-3-methylbutanenitrile.

9. The compound according to claim 1 which is 2-(3,4-difluorophenyl)amino-2-(3-pyridyl)butanenitrile.

10. The compound according to claim 1 which is 2-(4-trifluoromethoxyphenyl)amino-2-(3-pyridyl)-butanenitrile.

11. The compound according to claim 1 which is 2-(3-chloro-4-trifluoromethoxyphenyl)amino-2-(3-pyridyl)butanenitrile.

12. An antifungal composition for agricultural use which comprises as an active ingredient, a fungicidally effective amount of a compound according to one of claims 1 to 3 or 4 in association with an agriculturally acceptable inert support or surface active agent, therefor.

13. A composition according to claim 12, which contains, in addition to the active ingredient, an inert support and/or a surface-active agent, which can be employed in agriculture.

14. A composition according to claim 13, which contains from 0.001% to 95% by weight of active ingredient and from 0 to 20% by weight of surface-active agent.

15. A method for treating plants against phytopathogenic fungi which consists in applying to these plants an effective quantity of a compound according to one of claims 1 to 3 or 4.

* * * * *